(12) United States Patent
Grunei

(10) Patent No.: US 6,451,061 B1
(45) Date of Patent: Sep. 17, 2002

(54) LEG PROSTHESIS WITH SWIVELING PROSTHETIC FOOT

(75) Inventor: Hans Grunei, Lübeck (DE)

(73) Assignee: Schutt & Grundei Orthopadietechnik GmbH (DE)

( * ) Notice: Subject to any disclaimer, the term of this patent is extended or adjusted under 35 U.S.C. 154(b) by 0 days.

(21) Appl. No.: 09/710,982

(22) Filed: Nov. 9, 2000

(30) Foreign Application Priority Data

Nov. 10, 1999 (DE) .......................... 199 53 972

(51) Int. Cl.⁷ .................................................. A61F 2/64
(52) U.S. Cl. ........................................................ 623/40
(58) Field of Search ............................. 623/40, 41, 42, 623/44

(56) References Cited

U.S. PATENT DOCUMENTS

| | | | | |
|---|---|---|---|---|
| 1,066,605 A | * | 7/1913 | Hanger | 623/44 |
| 1,071,230 A | * | 8/1913 | Hanger | 623/44 |
| 2,466,134 A | * | 4/1949 | Touson | 623/44 |
| 2,568,051 A | | 9/1951 | Catrains | |
| 2,568,053 A | | 9/1951 | Catrains | |
| 3,947,897 A | | 4/1976 | Owens | |
| 5,405,408 A | * | 4/1995 | Pitkin | 623/44 |
| 5,509,936 A | | 4/1996 | Rappoport et al. | |

FOREIGN PATENT DOCUMENTS

| | | |
|---|---|---|
| DE | 204585 | 9/1908 |
| DE | 475303 | 10/1927 |
| DE | 3634263 A1 | 4/1988 |
| DE | 39 07 195 A1 | 9/1989 |
| DE | 19845191 | 3/2000 |
| EP | 0 358 056 B1 | 3/1990 |

* cited by examiner

Primary Examiner—Bruce Snow
(74) Attorney, Agent, or Firm—Cantor Colburn LLP

(57) ABSTRACT

The patent describes a leg prosthesis for adaptation to the stump of the upper leg, which is comprised of an adapter for a knee joint, a knee joint attached to it and a prosthetic lower leg coupled to the knee joint with a prosthetic foot coupled to it. It can be swiveled into the heel position, wherein the knee joint is designed so that when it moves from the extended position into the bent position, it makes a combined rolling/sliding movement on a swivel axis, in such a way that the distance from a point in front of the swivel axis when seen dorsally to the end of the prosthetic lower leg steadily decreases and from a point in front of the swivel axis seen ventrally to the end of the prosthetic lower leg steadily increases.

9 Claims, 2 Drawing Sheets

LEG PROSTHESIS WITH SWIVELING PROSTHETIC FOOT

TECHNICAL FIELD

This invention concerns a leg prosthesis for adaptation to a thigh stump. It is composed of an adapter for a knee joint, as is known from U.S. Pat. No. 3,947,897, for example. It is anchored with a post part in the stump of the femur. The adapter comes out of the thigh stump on the distal side, and there it can be coupled to an artificial knee joint, as is known from EP-B-0 358 056, for example.

BACKGROUND OF THE INVENTION

A prosthetic lower leg is usually coupled to the knee joint, and it in turn has a prosthetic foot attached on the distal side. The foot can be swiveled into the heel position.

In the proposal in EP-B-0 358 056, for example, the knee joint is designed so that it makes a combined rolling and sliding motion on a swivel axis when it goes from the extended position into the bent position. Unlike a purely hinged joint, the knee joint of the generic leg prosthesis is designed so that the distance from a point on the knee joint in front of the swivel axis, seen dorsally, to the end of the prosthetic lower leg steadily decreases. In other words, the distance from a point in front of the swivel axis, seen ventrally, on the other hand, to the end of the prosthetic lower leg steadily increases.

One problem for patients with partially amputated upper legs is, inter alia, that they have to walk with the healthy foot in a tip-of-the-foot position when they walk to allow the prosthetic foot to oscillate with the leg prosthesis when they take another step. This is true regardless of whether the prosthetic foot can now swivel on the prosthetic lower leg or is stopped tight to it. The need to put the healthy natural foot into a sharp or extreme tip-of-the-foot position, so that the prosthesis can oscillate, requires a very non-physiologic way of moving and thus puts a lot of stress on the spinal column when walking along.

SUMMARY OF THE INVENTION

On this background, the problem of this invention is to create an aide here, i.e., to further develop a generic leg prosthesis so there is no longer any need to put the healthy natural foot in a non-physiologic tip-of-the-foot position to allow the artificial leg to oscillate and so the motion seems more natural.

This problem is solved by placing a force-transmitting element between at least one mounting point in front of the swivel axis, seen from the dorsal side, and/or a mounting point in front of the swivel axis, seen from the ventral side, and the prosthetic foot, so the force-transmitting element moves the prosthetic foot when the knee joint is bent from the tip or mid-foot position of the artificial foot more into a heel position.

The knee movement thus actively controls a positioning force introduced into the prosthetic foot, in such a way that the more the knee bends, the more the prosthetic foot is put into the heel position. This shortens the stroke necessary for the healthy foot, and the leg prosthesis can oscillate slightly 5 to 10 mm in a way that allows the patient's motion to appear more natural.

The condition that the distance from a point in front of the swivel axis, seen from the dorsal side, to the end of the prosthetic lower leg steadily decreases is crucial. In a knee joint with a pure hinge joint, this condition would not exist, for example, The then given polar curve would also bring with it a displacement of the distance, for example, with the first movement from the extended position to the bent position. But after it reached a dead point, the distance would increase again. In a leg prosthesis, when the complete movement of the knee joint is executed from the extended position to the bent position, this would make the foot first swivel slightly into the heel position, after it exceeded the dead point mentioned, but it would be swiveled back into the starting or tip-of-the-foot position, so as a result when the knee joint is fully bent, there would again be a quasi-tip-of-the-foot position of the foot in relation to the prosthetic lower leg. But this is precisely the phenomenon to be avoided, so then there is no more need to bring the healthy foot more sharply into the tip-of-the-foot position so the leg prosthesis can oscillate.

One preferred embodiment provides that the force-transmission element be designed from a push rod jointed on the knee joint and on the prosthetic foot. On the proximal ends, the push rod can be jointed in the dorsal area of the knee joint, for example, in order to move the prosthetic foot from the starting position into the desired heel position while reducing the distance from the joint to the end of the prosthetic lower leg for the swivel movement.

The prosthetic foot is moved very reliably into the heel position when the knee joint moves from the extended position into the bent position, if the leg prosthesis is designed, as in one advantageous variation, so that the prosthetic foot is coupled to the prosthetic lower leg so it can swivel around a swivel point placed ventrally, and the force-transmission element is jointed on the prosthetic foot on a mounting point placed dorsally. The force-transmission element then causes torque around a mounting point placed dorsally, and the prosthetic foot swivels safely into the heel position.

Another preferred embodiment provides for flexible adjustable reins to be stretched to their effective length between the prosthetic foot and a bearing on the prosthetic lower leg, and the slack increases as the bending of the knee joint increases.

The reins basically do the work of the natural Achilles heel. The main job of the reins is to bring the foot back into its starting position when the knee joint is in the extended position. Because of the possibility of setting their effective length, for example with a threaded stop to which the end of the reins in question can be screwed, the reins are also used for individual adjustment of the tip-of-the-foot setting of the prosthetic foot. This adjustment generally differs with different heels from patient to patient.

A reset element is preferably built into the force-transmission element, and when the knee is extended, after being bent, it actively brings the prosthetic foot back into its starting position. This active reset element supports the effect of the reins mentioned above in the beginning movement from the bending position into the extended position of the knee. First, the force-transmission element mentioned triggers the reset effect, and the effect is triggered when the reins reach their extended position.

With the above-mentioned variation, it is preferred that the reset element have a guide case holding a spiral spring and a piston that goes into the case as part of the push rod, in such a way that, as the bending of the knee joint increases, the spring is put under increasing pressure and when the knee joint is extended, the spring force swivels the prosthetic foot into the starting position. The harder the knee is bent, the higher the spring forces that will be produced in the reset element.

Finally, it is advantageously provided that the guide case be mounted in a housing attached to the prosthetic lower leg. This produces a relatively standard compact unit for the patient to handle.

BRIEF DESCRIPTION OF THE DRAWINGS

The invention will be explained in greater detail below using the figures in the drawings.

The same reference numbers are used to identify the same items below.

DETAILED DESCRIPTION OF THE PREFERRED EMBODIMENT

Figure 1:
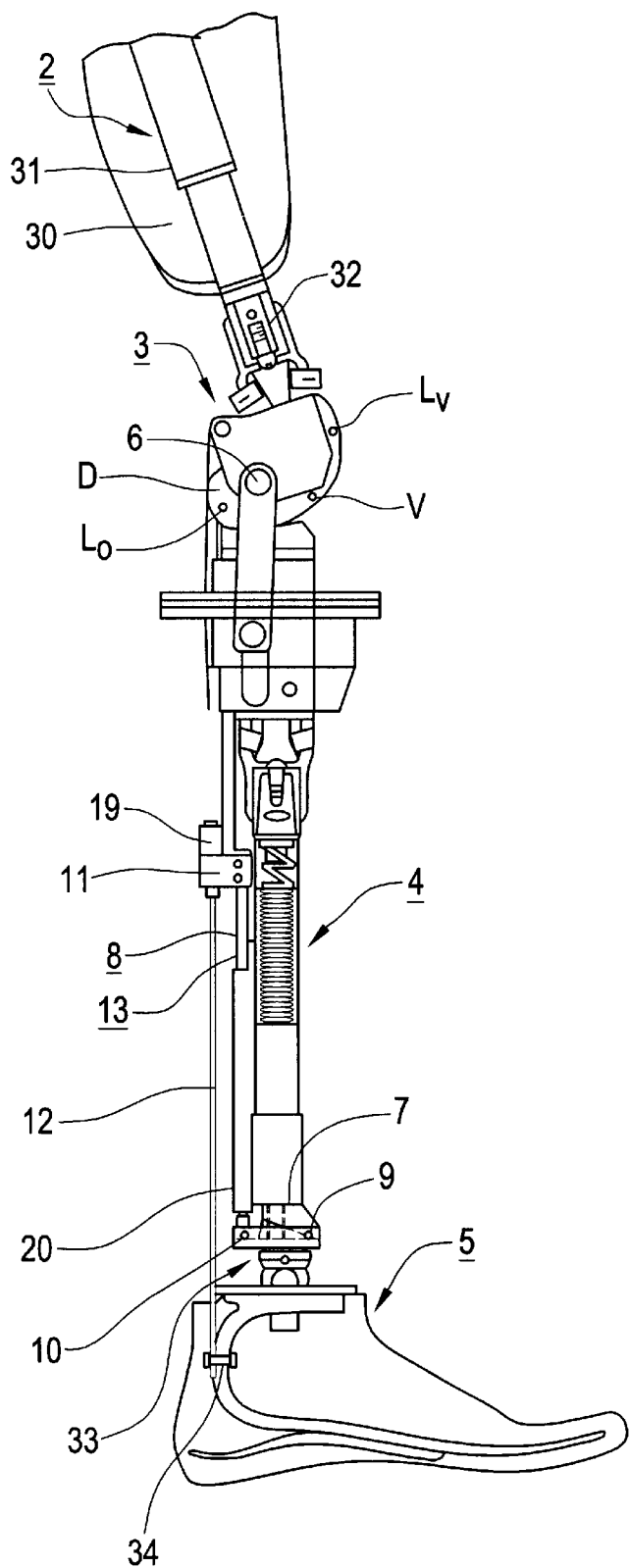
FIG. 1 shows a schematic side view of the complete leg prosthesis.

The leg prosthesis is composed of an adapter 2, which is connected to the upper leg 30 of the patient in such a way that the adapter 2 is attached to the stump 31 of the femur. A knee joint 3 is coupled to the coupling element 32 of the adapter 2, and is connected on the distal side to a prosthetic lower leg 4, which finally holds a prosthetic foot 5 in such a way that the prosthetic foot 5 is connected to the prosthetic lower leg 4 so it can swivel.

The knee joint 3 has a swivel axis 6, around which the upper part of the leg of the knee joint 3 can swivel in relation to the lower part 4 of the leg. The knee joint 3 has the special property that it makes a rolling/sliding motion during the transition from the extended position to the bent position on the swivel axis 6. This makes the distance from a point D, seen dorsally, in front of the swivel axis 6, to the end 7 of the prosthetic lower leg 4 steadily decrease. Said distance then increases steadily at a point V in front of the swivel axis 6, seen ventrally, when the knee joint 3 moves from the extended into the bent position.

The prosthetic foot 5 is jointed so it can swivel at the end 7 of the prosthetic lower leg 4 around a center of gravity 9 that is on the ventral side. If the prosthetic foot 5 swivels around swivel point 9, the prosthetic foot 5 goes into the heel position.

The movement of the knee joint 3 is coupled to the movement of the prosthetic foot 5 brought about by the force-transmission element 8, which is coupled to a mounting point Lo on the proximal side of the knee joint 3. Mounting point Lo is in front of swivel axis 6 when seen dorsally. Alternately or additionally, a force-transmission element can also be coupled to mounting point Lv in front of swivel axis 6 when seen ventrally. But then the force must be turned around by a roll mechanism, so that the force necessary to swivel the prosthetic foot 5 from the dorsal side can be introduced and the swivel movement around the swivel point 9 can be executed. The force of force-transmission element 8 is introduced dorsally into attachment 33 at mounting point 10.

Attachment 33 hereby takes over the function of the natural upper ankle joint.

The example of embodiment also has flexible reins 12 on the dorsal side between a bearing 11 attached to the prosthetic upper leg 4 and the prosthetic foot 5, here at mounting point 34. The reins 12 consist, for example, of a flexible apron that takes over the function of the natural Achilles heel. It is used to swivel the prosthetic foot 5 completely back into the starting position when the knee joint moves from the bent position into the extended position. It is also used for individual adjustment of the heel position of the prosthetic foot 5. For this, the reins 12 have a threaded case 17 on the proximal end that works with an attachment 19 with a thread inside and a bearing 11 in such a way that attachment 19 forms a stop on bearing 11. By screwing attachment 19 onto thread 35 (FIG. 2), the starting foot position (tip-of-the-foot setting) can be set individually by the patient.

Figure 2:
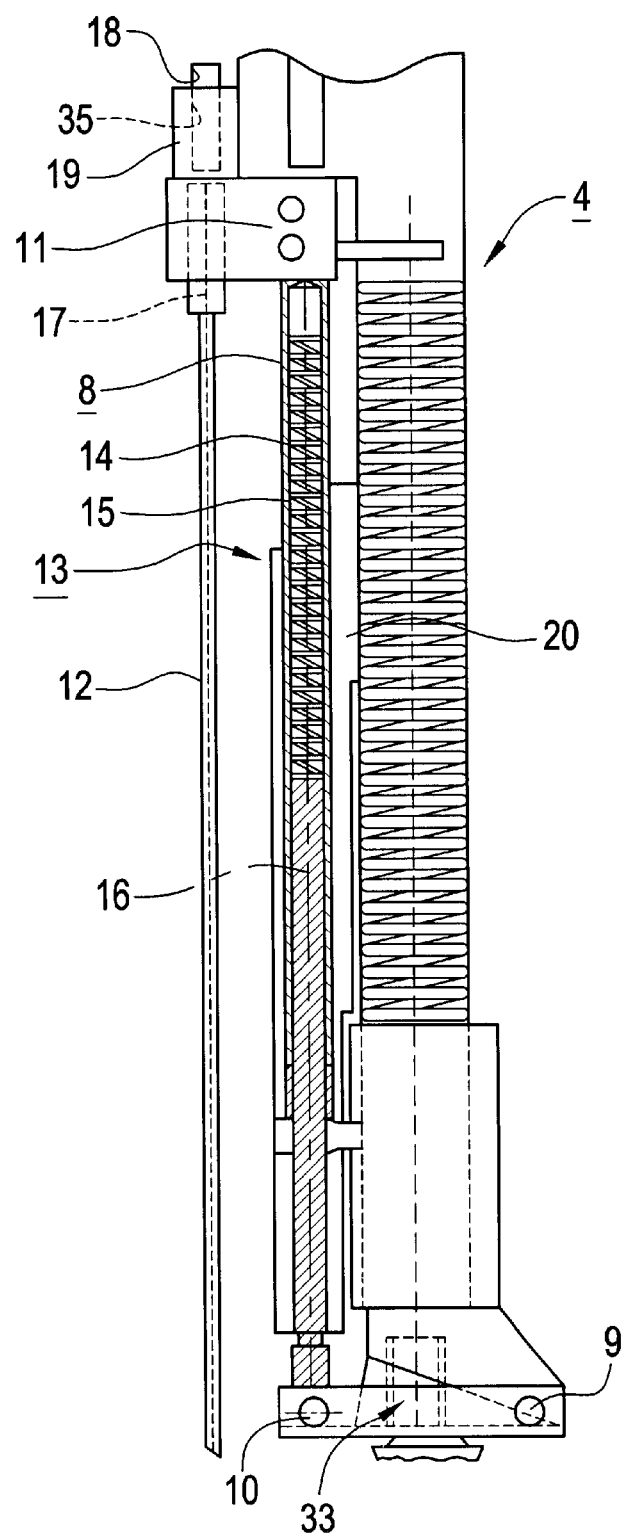
FIG. 2 shows a detailed view from FIG. 1, partially sectioned.

Other details are shown in FIG. 2.

Here, once again, there is a case 17 on the proximal end of the reins 12 with a thread 18 that works with attachment 19 and its inner thread 38.

The attachment here forms a stop element on bearing 11 connected to the prosthetic lower leg 4.

Here, a reset element 13 is built into the force-transmission element 8 that includes a guide case 15 in which there is a spiral spring 14. The guide case 15 with the spiral spring 14 works with a piston 16 that goes inside the case 15 in such a way that when there is a lot of force, the case 15 in FIG. 2 exerts increasing force down on the spring 14 in the case 15 as the bending movement increases. In reaction to this, the piston 16 transmits a corresponding force into attachment 33, and at mounting point 10, so the prosthetic foot 5 is forced to make a swivel movement around mounting point 9.

The important thing about the leg prosthesis in the invention is that a forced coupling is made here between the movement of the knee joint 3 and the swivel movement of the prosthetic foot 5. The condition for the steadily increasing swiveling of the prosthetic foot with the increasing bending position of the knee joint is the above-mentioned design of the knee joint, which must execute a rolling/sliding movement. Because of its geometry, a hinged knee joint cannot execute the desired swivel movement of the prosthetic foot.

What is claimed is:

1. A leg prosthesis for adaptation to a stump of an upper leg, the leg prosthesis comprising:
    an adapter for a knee joint;
    a knee joint attached to the adapter; and
    a prosthetic lower leg coupled to the knee joint with a prosthetic foot coupled to the prosthetic lower leg, the prosthetic foot can be swiveled into a heel position,
    wherein the knee joint is designed so that the knee joint makes a combined rolling/sliding movement when moving from an extended position into a bent position on a swivel axis,
    wherein a force-transmission element is arranged between a mounting point and the prosthetic foot, the mounting point is located at the knee joint, and the force-transmission element makes the prosthetic foot move increasingly from a tip-of-the-foot position into a heel position when the knee joint is bent.

2. The leg prosthesis in claim 1, wherein the force-transmission element has a push rod coupled to the knee joint and the prosthetic foot.

3. The leg prosthesis in claim 2 wherein the prosthetic foot is coupled to the prosthetic lower leg so the prosthetic foot can swivel around a ventral center of gravity and wherein the force-transmission element is coupled to the prosthetic foot on a dorsal mounting point.

4. The leg prosthesis in claim 1 wherein flexible reins adjusted to a selected length are stretched between the prosthetic foot and a bearing on the prosthetic lower leg, and the reins take increasing slack as the bending of the knee joint increases.

5. The leg prosthesis in claim 1 wherein a reset element is built into the force-transmission element, which when the knee joint is extended after first bending, the prosthetic foot moves back to the tip-of-the-foot position.

6. The leg prosthesis in claim 5, wherein the reset element has a guide case holding a spiral spring as well as a piston that goes into the guide case as part of a push rod, in such a way that as the knee joint increases its bend, increasing pressure is placed on the spiral spring and when the knee joint is extended, the spring force swivels the prosthetic foot into the tip-of-the-foot position.

7. The leg prosthesis in claim 6, wherein the guide case is mounted in a housing attached to the prosthetic lower leg.

8. The leg prosthesis in claim 1, wherein the mounting point is located in front of the swivel axis, when seen dorsally.

9. The leg prosthesis in claim 1, wherein the mounting point is located in front of the swivel axis, when seen ventrally.

* * * * *